(12) United States Patent
Goldberg et al.

(10) Patent No.: US 6,309,831 B1
(45) Date of Patent: Oct. 30, 2001

(54) METHOD OF MANUFACTURING BIOLOGICAL CHIPS

(75) Inventors: Martin J. Goldberg, Saratoga; Richard P. Rava, Redwood City, both of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/245,329

(22) Filed: Feb. 5, 1999

Related U.S. Application Data

(63) Continuation-in-part of application No. 09/019,882, filed on Feb. 6, 1998, now abandoned.

(51) Int. Cl.[7] .............................. C12Q 1/68; C12P 19/34; C12N 1/10; C07H 21/00; H01L 35/24

(52) U.S. Cl. .................. 435/6; 435/91.2; 435/283.1; 435/285.1; 435/287.2; 536/22.1; 536/23.1; 324/71.5; 324/73.1; 257/40; 257/414

(58) Field of Search ..................... 435/6, 91.2, 283.1, 435/285.1, 287.2; 536/23.1, 22.1; 437/1, 15, 53, 155; 324/73.1, 71.5; 257/414, 40

(56) References Cited

U.S. PATENT DOCUMENTS

| | | |
|---|---|---|
| 4,379,259 | 4/1983 | Varadi et al. . |
| 5,589,765 * | 12/1996 | Ohmart et al. ........... 324/158.1 |
| 5,798,556 | 8/1998 | Hughes et al. . |
| 5,843,655 | 12/1998 | McGall . |
| 5,856,101 | 1/1999 | Hubbell et al. . |
| 5,966,459 * | 10/1999 | Chen et al. ................ 382/149 |

FOREIGN PATENT DOCUMENTS

| | | |
|---|---|---|
| 0 695 941 | 5/1995 | (EP) . |
| 2 319 838 | 10/1997 | (GB) . |

OTHER PUBLICATIONS

Colom et al (IBMTDB vol. 18 No. 4 Sep. 1975.*
International Search Report (EPO Searching Authority) dated Jul. 1, 1999 re PCT/US99/02518.
O'Donnell–Maloney, Maryanne J. et al. "The development of microfabricated arrays for DNA sequencing and analysis" Tibtech Oct. 1996 (vol. 14), pp. 401–407.
Feldman, Klaus et al. "Closed Loop Quality Control in Printed Circuit Assembly "IEEE Transactions on Components, Hybrids, and Manufacturing Technology—Part A. vol. 17, No. 2 Jun. 1994, pp. 270–276.

* cited by examiner

*Primary Examiner*—Kenneth R. Horlick
*Assistant Examiner*—Jeffrey Siew
(74) *Attorney, Agent, or Firm*—Pamela Banner; Tom Evans; Philip McGarrigle

(57) ABSTRACT

A method of manufacturing items in parallel. Selected samples of items to be manufactured are subjected to additional steps in a manufacturing process. If such sample items meet the requisite quality control standard, remaining items are subjected to further manufacturing steps. If the sample items which have been further processed do not meet the requisite quality control standard, the lot from which the samples do not undergo the additional manufacturing step. Invention provides an improved method of manufacturing in that it prevents unnecessary manufacturing steps.

25 Claims, 5 Drawing Sheets

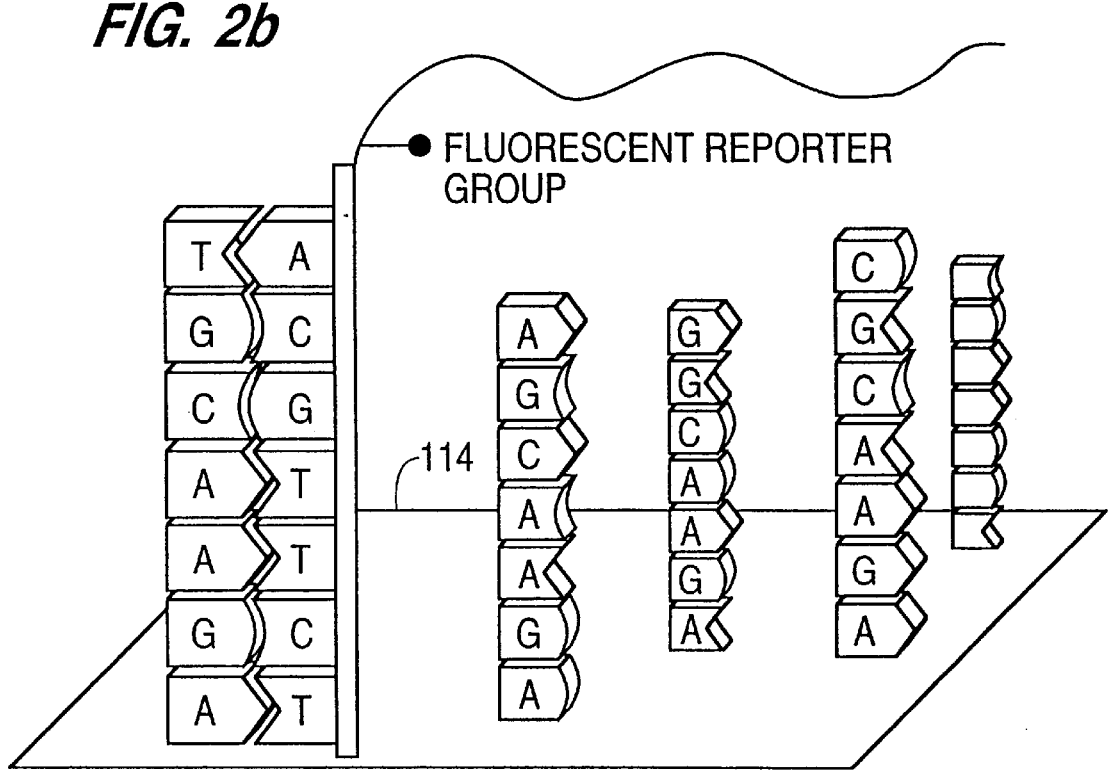

METHOD OF MANUFACTURING BIOLOGICAL CHIPS

CROSS-REFERENCE OF APPLICATION

This application is a continuation-in-part application of U.S. patent application Ser. No. 09/019,882, filed on Feb. 6, 1998, now abandoned.

BACKGROUND OF THE INVENTION

In most manufacturing in parallel scenarios, items to be manufactured must undergo a number of processing steps in order to obtain a finished product. Manufacturing of quantities of items in parallel requires that a representative group of the items manufactured undergo quality control testing in order to assure that the entire lot passes the appropriate standard. Typically, the quality control testing of the items to be manufactured is performed at the point the item of manufacture is completed. In the event that the representative sample of items fails the requisite standards, all the items that had been processed with samples which would be expected to have similar defects are rejected. When the basis for rejection exists because of a process which occurred several steps prior to the completion of the product, the further processes were performed unnecessarily, at a great expense of time and money.

SUMMARY OF THE INVENTION

This invention allows one to perform the quality control testing of items manufactured in parallel at a point before completion of the item or at a point when a further expensive processing step is necessary. Only samples of the product are processed to completion for quality control testing. If the completed products are rejected at this point, the time, effort and expense of performing the additional processing step(s) on the otherwise uncompleted products is avoided. If the items to be further processed have met the relevant quality control standard then the further processing can be accomplished with an expectation that the items meet the requisite standard thus far. Consequently, this invention allows for more effective use of resources.

This invention provides a method for manufacturing a plurality of items in parallel by first selecting a sample of the manufactured items from the plurality undergoing a process and subject this sample to further processing. The quality of the selected sample is subsequently determined, and if found to be satisfactory, the remainder of the items are subjected to further processing. The items of manufacture in the disclosed invention, for example, can be chips on a wafer. The further processing in this example can consist of the packaging of the chips. The chips can be biological chips composed of DNA, RNA, amino acids or analogs by thereof. This invention further provides a method for manufacturing arrays of necleic acids by fabricating a plurality of nucleic acid arrays on a substrate, separating the arrays, packaging a selected sample of the arrays, testing the selected sample and packaging the remaining arrays if the selected sample of arrays pass the testing step. The arrays of nucleic acid may be manufactured by, inter alia, light directed synthesis, nucleic acid spotting, or jet synthesis. The arrays on the substrate may be separated by sawing or scribing. Advantageous points in the process of array fabrication are useful for employing the method of the present invention.

BRIEF DESCRIPTION OF THE DRAWINGS

FIG. 2B illustrates conceptually the binding of probes on chips;

DETAILED DESCRIPTION

Figure 1:
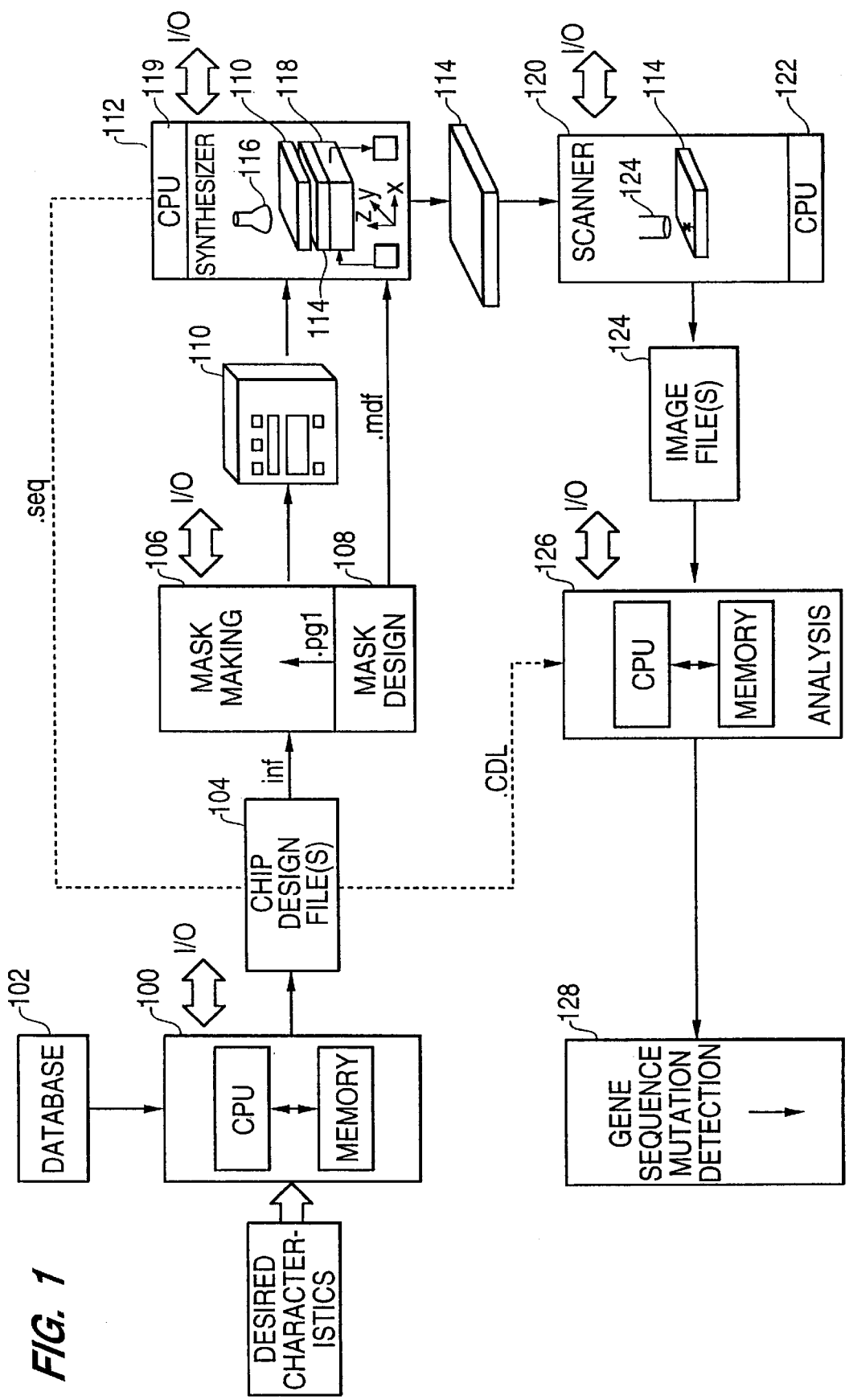
FIG. 1 illustrates the overall system and method of operation for array fabrication.

In manufacturing arrays of biological materials such as RNA or DNA, it is also desirable to avoid the performance of unnecessary steps. FIG. 1 illustrates a computerized system for forming and analyzing arrays of biological materials, such as RNA or DNA. A computer 100 is used to design arrays of biological polymers such as RNA or DNA. The computer 100 may be, for example, an appropriately programmed Sun Workstation or personal computer or work station, such as an IBM PC equivalent, including appropriate memory and a CPU. The computer system 100 obtains inputs from a user regarding desired characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 1, such equipment may or may not be located at the same physical site, but is shown together for ease of illustration in FIG. 1. The system 106 generates masks 110 such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed digital computer 119, which may or may not be the same computer as the computer(s) used in mask design and mask making.

The substrates fabricated by synthesis system 112 are optionally diced into smaller chips and exposed to marked receptors. The receptors may or may not be complementary to one or more of the molecules on the substrate. The receptors are marked with a label such as a fluorescein label (indicated by an asterisk in FIG. 1) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled receptor (*) has bound to the substrate. The output of scanner 120 is an image file(s) 124 indicating, in the case of fluorescein labeled receptor, the fluorescence intensity (photon counts or other related measurements, such as voltage) as a function of position on the substrate. Since higher photon counts will be observed where the labeled receptor has bound more strongly to the array of polymers, and since the monomer sequence of the polymers on the substrate is known as a function of position, it becomes possible to determine the sequence(s) of polymer(s) on the substrate that are complementary to the receptor.

The image file 124 is provided as input to an analysis system 126. Again, the analysis system may be any one of a wide variety of computer system(s), but in a preferred embodiment the analysis system is based on a Sun Workstation or equivalent. Using information regarding the molecular sequences obtained from the chip design files and the image files, the analysis system performs one or more of a variety of tasks. In one embodiment the analysis system compares the patterns of fluorescence generated by a receptor of interest to patterns that would be expected from a "wild" type receptor, providing appropriate output 128. If the pattern of fluorescence matches (within limits) that of the wild type receptor, it is assumed that the receptor of interest is the same as that of the wild type receptor. If the pattern of fluorescence is significantly different than that of the wild type receptor, it is assumed that the receptor is not wild type receptor. The system may further be used to identify specific mutations in a receptor such as DNA or RNA, and may in some embodiments sequence all or part of a particular receptor de novo.

Figure 2A:
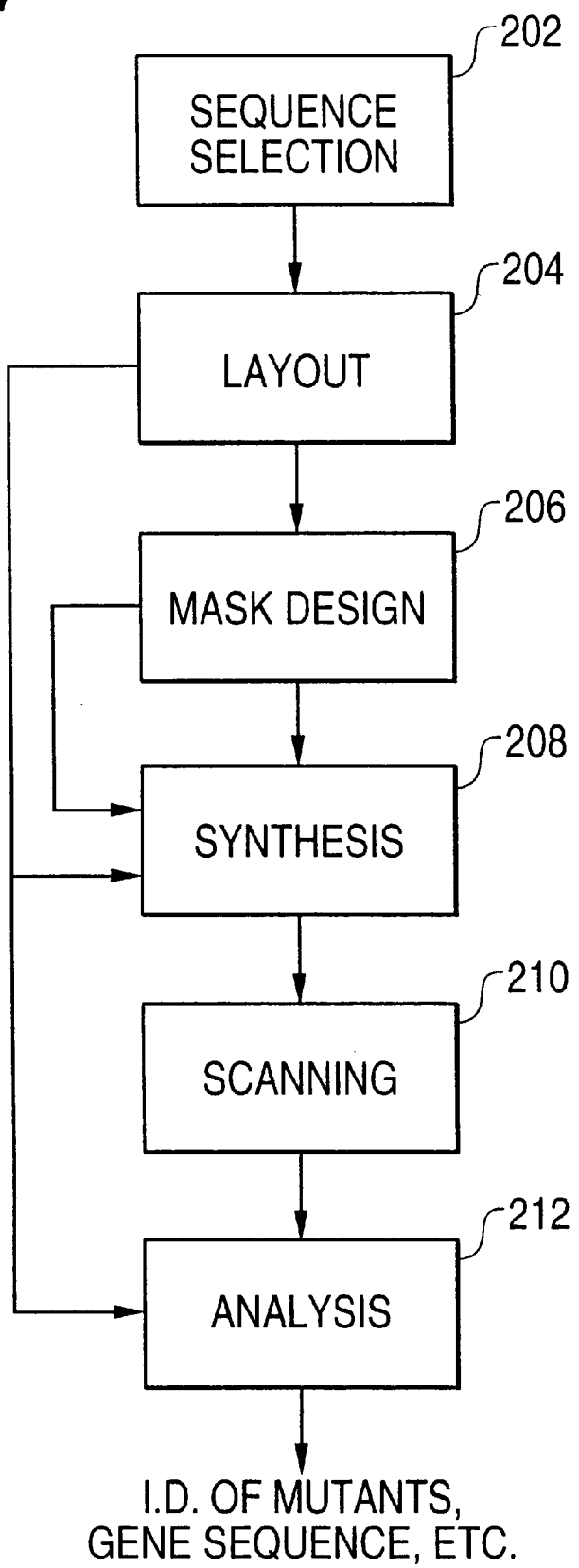
FIG. 2A is an illustration of the overall operation of the software involved in the system of FIG. 1.

FIG. 2A provides a simplified illustration of the software system used in operation of one embodiment of the invention. As shown in FIG. 2A, the system first identifies the genetic sequencer(s) that would be of interest in a particular analysis at step 202. The sequences of interest may, for example, be normal or mutant portions of a gene, genes that identify heredity, provide forensic information, or the like. Sequence selection may be provided via manual input of text files or may be from external sources such as GenBank. At step 204 the system evaluates the gene to determine or assist the user in determining which probes would be desirable on the chip, and provides an appropriate "layout" on the chip for the probes. The layout will implement desired characteristics such as minimization of edge effects, ease of synthesis, and/or arrangement on the chip that permitts "reading" of genetic sequence.

At step 206 the masks for the synthesis are designed. Again, the masks will be designed to implement one or more desired attributes. For example, the masks may be designed to reduce the number of masks that will be needed, reduce the number of pixels that must be "opened" on the mask, and/or reduce the number of exposures required in synthesis of the mask, thereby reducing cost substantially.

At step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled receptor.

The software controls the scanning of the chip, and stores the data thus obtained in a file that may later be utilized to extract sequence information.

At step 212 the software system utilizes the layout information and the fluorescence information to evaluate the chip. Among the important pieces of information obtained from DNA chips are the identification of mutant receptors, and determination of genetic sequence of a particular receptor.

FIG. 2B illustrates the binding of a particular target DNA to an array of DNA probes 114. As shown in this simple example, the following probes are formed in the array:

3'-AGAACGT

AGAACGA

AGAACGG

AGAACGC . . .

When a fluorescein-labeled (or other marked) target with the sequence 5'-TCTTGCA is exposed to the array, it is complementary only to the probe 3'-AGAACGT, and fluorescein will be found on the surface of the substrate where 3'-AGAACGT is located. By contrast, if 5'-TCTTGCT is exposed to the array, it will bind only (or most strongly) to 3'-AGAACGA. By identifying the location where a target hybridizes to the array of probes most strongly, it becomes possible to extract sequence information from such arrays using the invention herein.

New technology, called VLSIPS®, has enabled the production of chips smaller than a thumbnail that contain hundreds of thousands or more of different molecular probes. These techniques are described in U.S. Pat. No. 5,143,854, PCT WO 92/10092, and PCT WO 90/15070, which are herein incorporated by reference in their entireties for all they disclose. Biological chips have probes arranged in arrays, each probe ensemble assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips are useful in a variety of screening techniques for obtaining information about either the probes or the target molecules. For example, a library of peptides can be used as probes to screen for drugs. The peptides can be exposed to a receptor, and those probes that bind to the receptor can be identified.

Biological chips wherein the probes are oligonucleotides ("oligonucleotide arrays") show particular promise. Arrays of nucleic acid probes can be used to extract sequence information from nucleic acid samples. The samples are exposed to the probes under conditions that allow hybridization. The arrays are then scanned to determine to which probes the sample molecules have hybridized. One can obtain sequence information by selective tiling of the probes with particular sequences on the arrays, and using algorithms to compare patterns of hybridization and non-hybridization. This method is useful for sequencing nucleic acids. It is also useful in diagnostic screening for genetic diseases or for the presence of a particular pathogen or a strain of pathogen.

The scaled-up manufacturing of oligonucleotide arrays requires application of quality control standards both for determining the quality of chips under current manufacturing conditions and for identifying optimal conditions for their manufacture. Quality control, of course, is not limited to manufacture of chips, but also to the conditions under which they are stored, transported and, ultimately, used.

U.S. Pat. No. 5,384,261 is directed to a method and device for forming large arrays of polymers on a substrate and is hereby incorporated by reference in its entirety for all it discloses. According to a preferred aspect of the invention, the substrate is contacted by a channel block having channels therein. Selected reagents are flowed through the channels, the substrate is rotated by a rotating stage, and the process is repeated to form arrays of polymers on the substrate. The method may be combined with light-directed methodolgies.

More specifically, U.S. Pat. No. 5,384,261 describes a method and system for synthesizing arrays of diverse polymer sequences. According to a specific aspect of the invention, a method of synthesizing diverse polymer sequences such as peptides or oligonucleotides is provided. The diverse polymer sequences may be used, for example, in screening studies for determination of binding affinity.

Methods of synthesizing desired polymer sequences such as peptide sequences are well known to those of skill in the art. For example, the so-called "Merrifield" solid-phase peptide synthesis has been in common use for several years and is described in Merrifield, J. Am. Chem Soc. (1963) 85:2149–2154, incorporated herein by reference for all purposes. Solid-phase peptide synthesis techniques have been extended to provide for the synthesis of several peptide sequences on, for example, a number of "pins" as described in, for example, Geysen et. al., J. Immun. Meth. (1987) 102:259–274, also incorporated herein by reference for all purposes. Methods of synthesizing oligonucleotides are found in, for example, Oligonucleotide Synthesis: A Practical Approach, Gait, ed., IRL Press, Oxford (1984), incorporated herein by reference in its entirety for all purposes.

Such methods and devices have continued to be limited in the number of sequences which can be synthesized in a reasonable amount of time. For example, Geysen et. al. report in the above journal that it has taken approximately 3 years to synthesize 200,000 peptide sequences. Such methods have continued to produce fewer peptide sequences for study than are often desired.

Techniques for forming sequences on a substrate are known. For example, the sequences may be formed according to the pioneering techniques disclosed in U.S. Pat. No. 5,143,854 (Pirrung et al.), PCT WO 92/10092, or U.S. patent application Ser. No. 08/249,188 filed May 24, 1994, now U.S. Pat. No. 5,571,639, Nov. 5, 1996 incorporated herein by reference for all purpose. The prepared substrates will have a wide range of applications. For example, the substrates may be used for understanding the structure-activity relationship between different materials or determining the sequence of an unknown material. The sequence of such unknown material may be determined by, for example, a process known as sequencing by hybridization. In one method of sequencing by hybridization, a sequences of diverse materials are formed at known locations on the surface of a substrate. A solution containing one or more targets to be sequenced is applied to the surface of the substrate. The targets will bind or hybridize with only complementary sequences on the substrate.

The locations at which hybridization occurs can be detected with appropriate detection systems by labelling the targets with a fluorescent dye, radioactive isotope, enzyme, or other marker. Exemplary systems are described in U.S. Pat. No. 5,143,854 (Pirrung et al.) and U.S. patent application Ser. No. 08/143,312, now abandoned, also incorporated herein by reference for all purposes. Information regarding target sequences can be extracted from the data obtained by such detection systems.

By combining various available technologies, such as photolithography and fabrication techniques, substantial progress has been made in the fabrication and placement of diverse materials on a substrate. For example, thousands of different sequences may be fabricated on a single substrate of about 1.28 $cm^2$ in only a small fraction of the time required by conventional methods. Such improvements make these substrates practical for use in various applications, such as biomedical research, clinical diagnostics, and other industrial markets, as well as the emerging field of genomics, which focuses on determining the relationship between genetic sequences and human physiology. As commercialization of such substrates becomes widespread, an economically feasible and high-throughput device and method for packaging the substrates are desired.

As noted above, the substrates may be diced into smaller chips and packaged. Economical and efficient packaging devices for a substrate having an array of probes fabricated thereon have been developed. The probe arrays may be fabricated according to the pioneering techniques disclosed in U.S. Pat. No. 5,143,854 (Pirrung et al.), PCT WO 92/10092, or U.S. application Ser. No. 08/249,188 filed May 24, 1994, now U.S. Pat. No. 5,571,639 Nov. 5, 1996, already incorporated herein by reference for all purposes. According to one aspect of the techniques described therein, a plurality of probe arrays are immobilized at known locations on a large substrate or wafer.

A typical wafer may be populated with numerous probe arrays. The wafer may be composed of a wide range of material, either biological, nonbiological, organic, inorganic, or a combination of any of these, existing as particles, strands, precipitates, gels, sheets, tubing, spheres, containers, capillaries, pads, slices, films, plates, slides, etc. The wafer may have any convenient shape, such as a disc, square, sphere, circle, etc. The wafer is preferably flat but may take on a variety of alternative surface configurations. For example, the wafer may contain raised or depressed regions on which a sample is located. The wafer and its surface preferably form a rigid support on which the sample can be formed. The wafer and its surface are also chosen to provide appropriate light-absorbing characteristics. For instance, the wafer may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly) vinylidenedifluoride, polystyrene, polycarbonate, or combinations thereof. Other materials with which the wafer can be composed of will be readily apparent to those skilled in the art upon review of this disclosure. In a preferred embodiment, the wafer is flat glass or single-crystal silicon.

Surfaces on the solid wafer will usually, though not always, be composed of the same material as the wafer. Thus, the surface may be composed of any of a wide variety of materials, for example, polymers, plastics, resins, polysaccharides, silica or silica-based materials, carbon, metals, inorganic glasses, membranes, or any of the above-listed wafer materials.

The wafer includes a plurality of marks that are located in streets (area adjacent to the probe arrays). Such marks may be used for aligning the masks during the probe fabrication process. In effect, the marks identify the location at which each array is to be fabricated. The probe arrays may be formed in any geometric shape. In some embodiments, the shape of the array may be squared to minimize wasted wafer area. After the probe arrays have been fabricated, the wafer is separated into smaller units known as chips. The wafer, for example, may be about 5×5 inches on which 16 probe arrays, each occupying an area of about 12.8 cm², are fabricated.

As noted, a chip may be separated from the wafer. For example, a chip may contain a probe array and a plurality of alignment marks. The marks serve multiple functions, such as: 1) aligning the masks for fabricating the probe arrays, 2) aligning the scriber for separating the wafer into chips, and 3) aligning the chip to the package during the attachment process. In some embodiments, such chips may be of the type known as Very Large Scale Immobilized Polymer Synthesis (VLSIPS™) chips.

According to a specific embodiment, the chip contains an array of genetic probes, such as an array of diverse RNA or DNA probes. In some embodiments, the probe array will be designed to detect or study a genetic tendency, characteristic, or disease. For example, the probe array may be designed to detect or identify genetic diseases such as cystic fibrosis or certain cancers (such as P53 gene relevant to some cancers), as disclosed in U.S. patent application Ser. No. 08/143,312, now abandoned already incorporated by reference.

The wafer is separated into a plurality of chips using a technique known as scribe and break. A fully programmable computer may be used to control scribe and break of the device, which in some embodiments may be a DX-III Scriber breaker manufactured by Dynatex International.® The device may include a base with a rotation stage on which a wafer is mounted. The rotation stage includes a vacuum chuck for fixing the wafer thereon. A stepper motor, which is controlled by the system, rotates stage. Located above the stage is a head unit that includes a camera and cutter. Head unit is mounted on a dual-axis frame. The camera generates an image of the wafer on video display. The video display includes a cross hair alignment mark. The camera, which includes a zoom lens and a fiber optic light, allows a user to inspect the wafer on the video display. A control panel is located on the base for operating device.

Once the cutter is aligned, the user instructs the device to scribe the wafer. In some embodiments, various options are available to the user, such as scribe angle, scribe pressure, and scribe depth. These parameters will vary depending on the composition and/or thickness of the wafer. Preferably, the parameters are set to scribe and break the wafer without causing any damage thereto or penetrating through the frame. The device repeatedly scribes the wafer until all the streets in one axis have been scribed, which in one embodiment is repeated 5 times (a 4×4 matrix of probe arrays). The user then rotates the stage 90° to scribe the perpendicular streets.

Once the wafer has been scribed, the user instructs the device to break or separate the wafer into chips. The shock from the impulse bar fractures the wafer along the scribe. Since most of the force is dissipated along the scribe, device 200 is able to produce high breaking forces without exerting significant forces on the wafer. Thus, the chips are separated without causing any damage to the wafer. Once separated, the chips are then packaged. Of course, other more conventional techniques, such as the sawing technique disclosed in U.S Pat. No. 4,016,855, incorporated herein by reference for all purposes, may be employed.

Methods for synthesizing a variety of different types of polymers are well known in the art. For example, the "Merrifield" method, described in Atherton et al., "Solid Phase Peptide Synthesis," IRL Press, 1989, which is incorporated herein by reference for all purposes, has been used to synthesize peptides on a solid support. In the Merrifield method, an amino acid is covalently bonded to a support made of an insoluble polymer or other material. Another amino acid with an alpha protecting group is reacted with the covalently bonded amino acid to form a dipeptide. After washing, the protecting group is removed and a third amino acid with an alpha protecting group is added to the dipeptide. This process is continued until a peptide of a desired length and sequence is obtained.

Methods have also been developed for producing large arrays of polymer sequences on solid substrates. These large "arrays" of polymer sequences have wide ranging applications and are of substantial importance to the pharmaceutical, biotechnology and medical industries. For example, the arrays may be used in screening large numbers of molecules for biological activity, i.e., receptor binding capability. Alternatively, arrays of oligonucleotide probes can be used to identify mutations in known sequences, as well as in methods for de novo sequencing of target nucleic acids.

Of particular note, is the pioneering work described in U.S. Pat. No. 5,143,854 (Pirrung et al.) and PCT Application No. 92/10092 disclose improved methods of molecular synthesis using light directed techniques. According to these methods, light is directed to selected regions of a substrate to remove protecting groups from the selected regions of the substrate. Thereafter, selected molecules are coupled to the substrate, followed by additional irradiation and coupling steps. By activating selected regions of the substrate and coupling selected monomers in precise order, one can synthesize an array of molecules having any number of different sequences, where each different sequence is in a distinct, known location on the surface of the substrate.

These arrays clearly embody the next step in solid phase synthesis of polymeric molecules generally, and polypeptides and oligonucleotides, specifically. Accordingly, it would be desirable to provide methods for preparation of these arrays, which methods have high throughput, high product quality, enhanced miniaturization and lower costs. The present invention meets these and other needs.

Novel processes have been developed for the efficient, large scale preparation of arrays of polymer sequences wherein each array includes a plurality of different, positionally distinct polymer sequences having known monomer sequences. It is known to perform cleaning and stripping of substrate wafers to remove oil and dirt from the surface, followed by the derivatization of the wafers to provide photoprotected functional groups on the surface. Polymer sequences are then synthesized on the surface of the substrate wafers by selectively exposing a plurality of selected regions on the surface to an activation radiation to remove the photolabile protecting groups from the functional groups and contacting the surface with a monomer containing solution to couple monomers to the surface in the selected regions. The exposure and contacting steps are repeated until a plurality of polymer arrays are formed on the surface of the substrate wafer. Each polymer array includes a plurality of different polymer sequences coupled to the surface of the substrate wafer in a different known location. The wafers are then separated into a plurality of individual substrate segments, each segment having at least one polymer array formed thereon, and packaged in a cartridge whereby the surface of said substrate segment having the polymer array formed thereon is in fluid contact with the cavity.

In U.S. Pat. No. 5,843,655, herein incorporated by reference in its entirety for all purposes, methods for testing oglionucleotide arrays are provided. As disclosed in the '655 patent, methods are provided for testing the quality of biological chips and the effect of various parameters used in their production by manufacturing oligonucleotide arrays by spatially directed oligonucleotide synthesis in high volume and testing selected arrays. In one embodiment the methods involve determining the extent to which a test condition causes the appearance of a structural feature in oligonucleotides produced on an oligonucleotide array by spatially directed oligonucleotide synthesis by providing a substrate having a surface with linkers having an active site for oligonucleotide synthesis; synthesizing an ensemble of sequence-specific oligonucleotides on the substrate by spatially directed oligonucleotide synthesis, the oligonucleotides optionally having active sites for attaching a detectable label; exposing the area to the test condition; and determining the amount of oligonucleotides having the structural feature.

Figure 3:
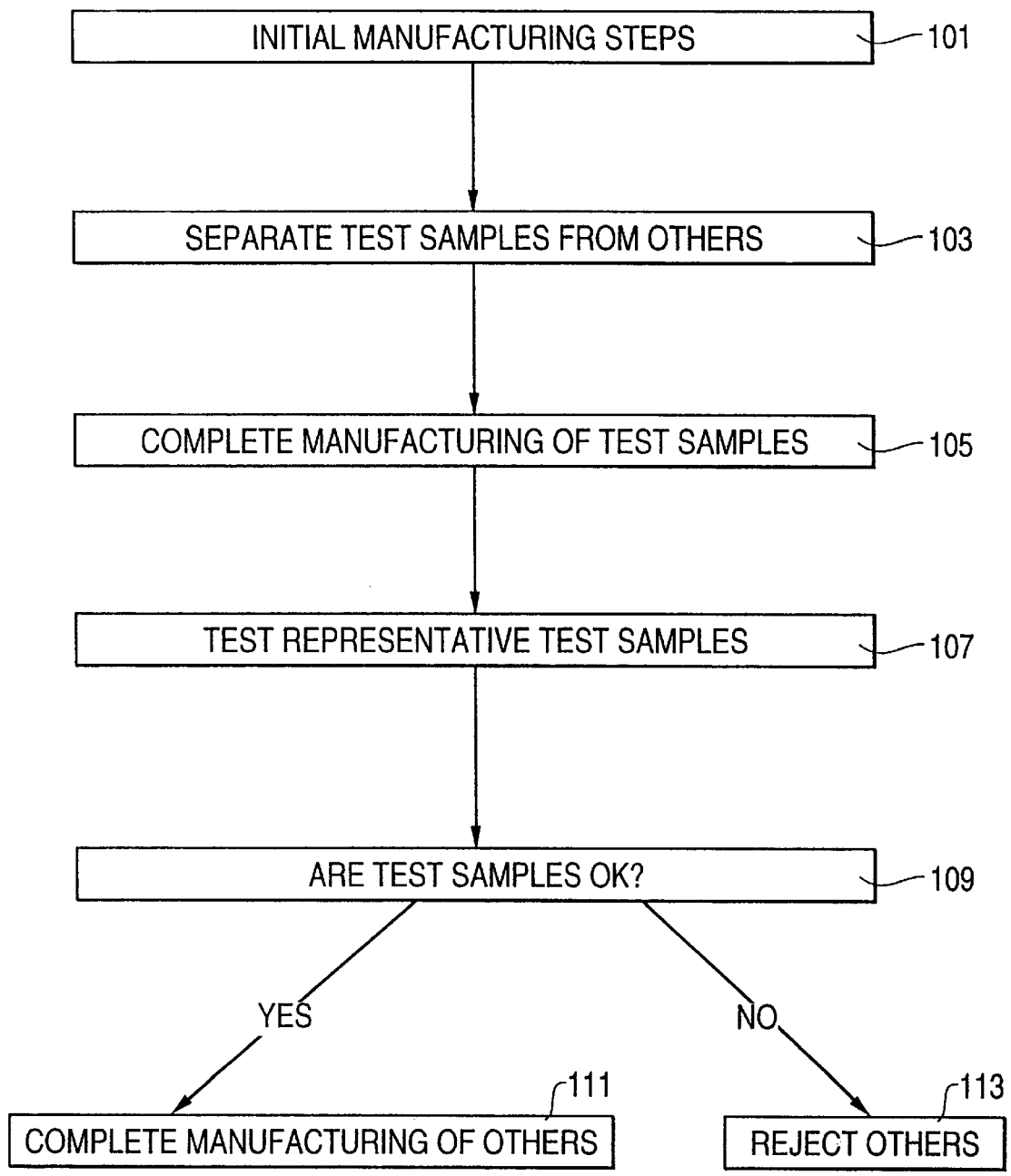
FIG. 3 illustrates an overall flowchart for the invention.

FIG. 3 is an overall flow chart illustrating one embodiment of the invention. At step 101 initial manufacturing processes are completed upon items under manufacture. At step 103 a sample portion of the items is separated for testing. The sample should be sufficiently large to give a level of confidence that any defects in the items will be detected in the samples. At step 105 additional manufacturing steps are performed on the sample items. At step 107 quality control testing is performed on the sample items. At step 109 it is determined if the sample items were adequate to pass a quality control standard. If they do, the remaining items are completed in the manufacturing process at step 111. If the sample items were not adequate, the remaining items are also rejected at step 113, avoiding the need to complete the manufacturing process in such items.

The process herein will be applicable to a wide variety of manufactured items such as, for example, certain semiconductor devices where it may be assumed that if one or a few chips in a wafer are adequate, the remaining chips on a wafer are adequate. A particular application of the invention is found in manufactured devices comparing biological such as arrays of nucleic acids or peptides, such as disclosed in U.S. Pat. No. 5,143,854, incorporated herein by reference for all purposes. In alternative embodiments, the arrays are composed of inorganic materials such as phosphorus, catalysts, or the like. See Schuly et al, WO 96/1878 incorporated herein by reference.

An example of the current invention is in the field of testing and packaging biological chips in wafers. Currently, biological chips are manufactured in individual wafers. For example, a single wafer may be comprised of between 4 to 400 biological chips. Methods for testing biological chips on a wafer after all the chips have been diced and packaged are described in, for example, McGall et al, U.S. Pat. No. 5,843,655, now U.S. Pat. No. 5,843,655 Nov. 1, 1998, incorporated herein by reference. After a wafer with biological chips is manufactured, individual chips are diced from the wafer and selected arrays (e.g. 2–5 arrays) are placed in appropriate cartridges. These selected arrays (or "chips") are tested. If the tested chips from a particular wafer meet the designated quality control standards then all the chips on that wafer are accepted and the remaining arrays are processed. However, if the tested chips have not met the appropriate quality control standard then all the packaged chips from the tested wafer are rejected and the remaining chips are not packaged. Consequently the resources necessary to package the biological chips are reserved for chips which have passed the quality control standards. The intervening quality control step may immediately precede any major downstream processing step. Thus there is assurance that the chips being further processed have met the appropriate quality standard prior to the further processing.

Another example of the current invention is in the field of cloning and preparation of substrates prior to chip synthesis. In this case synthesis of a particular test vehicle or some other analytical or functional test of the of the substrate would be done prior to doing normal array synthesis on the remaining wafers. More specifically, substrate surfaces are first prepared and coated with silane. If, after these first two intial steps, the substrate is tested and fails, the entire batch of substrates from which the tested substrate was supplied will be discarded.

Figure 4:
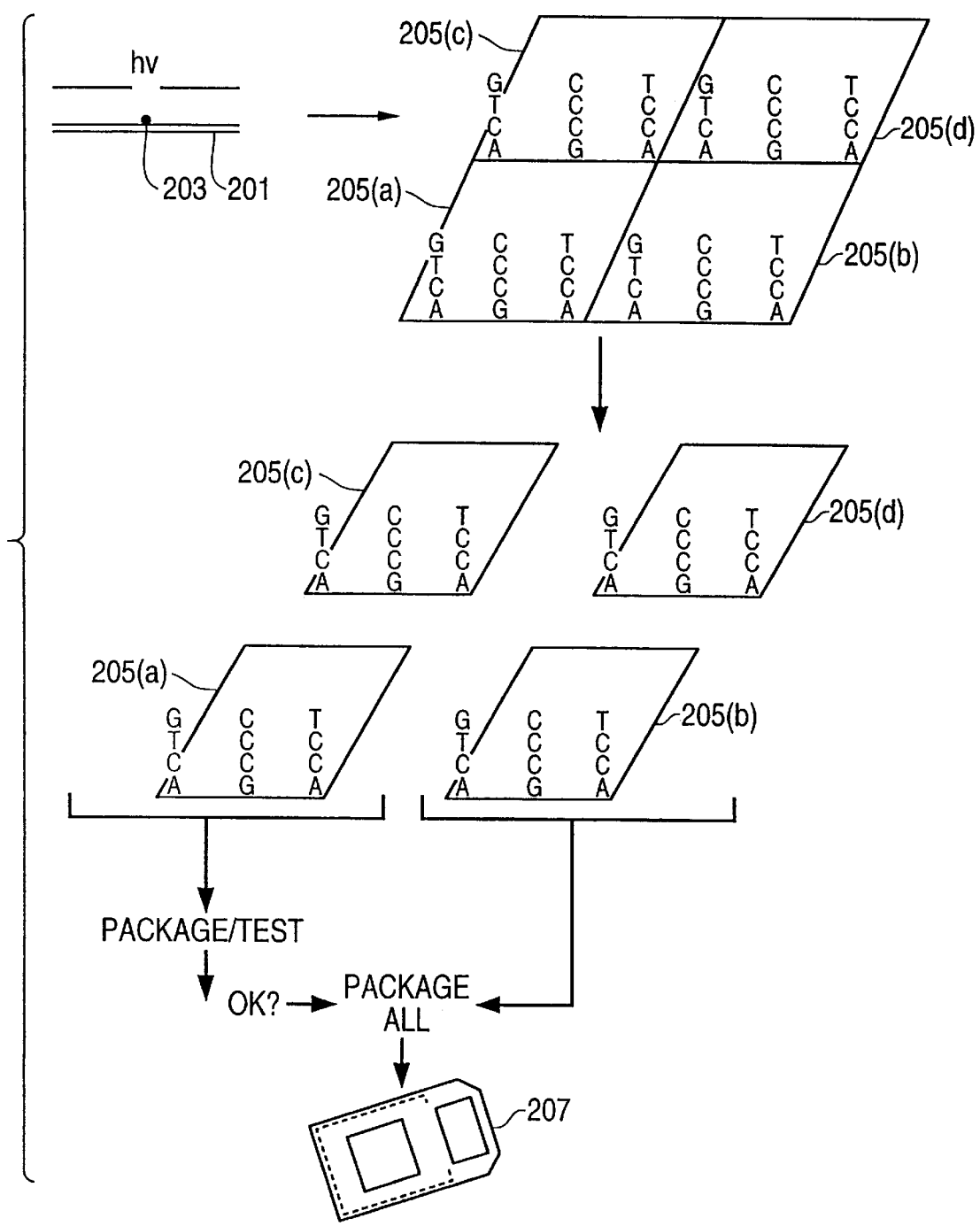
FIG. 4 is an example of the invention used in the manufacture of nucleic acid probe arrays.

FIG. 4 illustrates a particular embodiment of the invention used in the manufacture of nucleic acid arrays. As shown, a substrate 201 is exposed, in this case, to light for activation of a region 203. The process is repeated with other exposed regions and nucleic acid building block to form multiple identical arrays 205(a), 205(b), 205(c), and 205(d) on the substrate. While the light directed fabrication process is described herein by way of example, other processes, such as ink jet fabrication, spotting and other techniques may be useful in some embodiments.

Thereafter, the substrate is diced by, for example, sawing or scribing into individual chips or arrays 205(a), 205(b), 205(c), and 205(d). One or a few of the arrays 205(a)and 205(b) are, for example, packaged in a chip holder such as described in PCT U.S. 96,11147, incorporated herein by reference. The packaged arrays are tested for quality and if they indicate that the wafer is acceptable, the remaining chips 205(b) and 205(d) are packaged to form packaged arrays 207.

It is to be understood that the above description is intended to be illustrative and not restrictive. The scope of the invention should, therefore, be determined not with reference to the above description but to the appended claims along with their full scope of equivalents.

What is claimed is:

1. A method for manufacturing a plurality of items in parallel comprising:
   selecting a sample of items from a plurality of items undergoing a manufacturing process;
   subjecting said sample to further manufacturing processing;
   identifying a quality of the selected sample; and
   if said quality is determined to be satisfactory, then subjecting the remainder of said items to said further processing.

2. The method of claim 1 wherein the plurality of the items to be manufactured are chips on a wafer.

3. The method of claim 2 wherein the chips include biological material.

4. The method of claim 3 wherein the biological material is selected from the group consisting of DNA, RNA, amino acids and analogs thereof.

5. The method of claim 2 wherein said further processing is packaging of the chips.

6. A method of manufacturing arrays of nucleic acids comprising:
   fabricating a plurality of duplicate nucleic acid always on a substrate;
   separating said plurality of arrays;
   finishing the manufacturing process of a selected sample of arrays from said plurality of arrays;
   testing said selected arrays; and
   if said selected sample of arrays pass said testing, completing the manufacturing of the remainder of said plurality of arrays.

7. The method of claim 6 wherein said arrays are manufactured by light directed synthesis.

8. The method of claim 6 wherein said arrays are manufactured by nucleic acid spotting.

9. The method of claim 6 wherein said arrays are made by ink jet synthesis.

10. The method of claim 6 wherein said arrays are separated by sawing.

11. The method of claim 6 wherein said arrays are separated by scribing.

12. The method of claim 1 wherein the plurality of items to be manufactured are substrates for synthesis of an array of materials.

13. The method of claim 12 wherein said further processing is the cleaving and preparation of of substrates.

14. A method of manufacturing arrays of biological materials comprising:

preparing a plurality of substrates;

fabricating arrays of biological materials on at least one of said substrates;

separating said arrays formed on said at least one of substrates;

selecting a sample of arrays;

packaging selected sample of said separated arrays;

testing said packaged arrays; and then subjecting the remainder of the substrates to the rest of the manufacturing process.

15. The method of claim 14 further comprising:

performing a first test on a sample of said substrates after said preparing step and, if said sample fails said first test step, discarding said substrates.

16. The method of claim 15 further comprising:

performing a second test on said at least one of said substrates after said fabricating step and, if said at least one of said substrates fails said second test, discarding said at least one of said substrates.

17. The method of claim 16 further comprising:

performing a third test on said arrays after said separating step and, if said arrays fail said third test, discarding said arrays.

18. The method of claim 17 further comprising:

performing a fourth test on said separated arrays after said packaging step and, if said separated arrays fail said fourth test, discarding said arrays.

19. The method of claim 18 further comprising:

performing a fifth test on said packaged arrays after said testing step and, if said packaged arrays fail said fifth step, discarding said arrays.

20. A method of manufacturing arrays of biological materials comprising:

preparing a plurality of substrates;

selecting a sample of said substrates;

testing said sample of substrates;

discarding any failed substrates after said testing step;

then subjecting the remainder of the substrates to the rest of the manufacturing process.

21. A method of manufacturing arrays of biological materials comprising:

preparing a plurality of substrates;

fabricating arrays of biological materials on at least one of said substrates;

testing a sample of said fabricated arrays of biological materials;

separating said arrays formed on said at least one of said substrates;

packaging selected sample of said separated arrays;

wherein said separating and packaging steps are performed only when said fabricated arrays pass said testing; and then subjecting the remainder of the substrates to the rest of the manufacturing process.

22. A method of manufacturing arrays of biological materials comprising:

preparing a plurality of substrates;

fabricating arrays of biological materials on at least one of said substrates;

separating said arrays formed on said at least one of said substrates;

testing a sample of said separated arrays;

packaging selected of said separated arrays;

wherein said packaging step is performed only when said separated arrays pass said testing; and then subjecting the remainder of the substrates to the rest of the manufacturing process.

23. The method of manufacturing arrays of biological materials recited in claim 20, wherein the step of prepared a plurality of substrates includes preparing surfaces on a plurality of substrates; and depositing silane on said substrate surfaces.

24. The method of manufacturing arrays of biological materials recited in claim 20, further including:

fabricating arrays of biological materials on at least one of said substrates;

separating said arrays formed on said at least one of said substrates;

packaging a selected sample of said separated arrays;

wherein said fabricating, separating, and packaging steps are performed only when said selected sample of said substrates pass said testing.

25. A method of manufacturing arrays of peptides comprising fabricating a plurality of duplicate peptide arrays on a substrate;

separating said plurality of arrays;

packaging selected sample of arrays from said plurality of arrays;

testing said selected arrays; and if said selected arrays pass said testing, packaging the remainder of the plurality of arrays.

\* \* \* \* \*

UNITED STATES PATENT AND TRADEMARK OFFICE
CERTIFICATE OF CORRECTION

PATENT NO.    : 6,309,831 B1                                    Page 1 of 1
DATED         : October 30, 2001
INVENTOR(S)   : Martin J. Goldberg et al.

It is certified that error appears in the above-identified patent and that said Letters Patent is hereby corrected as shown below:

Column 10,
Line 57, replace "always" with -- arrays --.

Signed and Sealed this

Twenty-second Day of April, 2003

JAMES E. ROGAN
*Director of the United States Patent and Trademark Office*